US00PP10789P

United States Patent [19]

Mennell et al.

[11] Patent Number: Plant 10,789

[45] Date of Patent: Feb. 16, 1999

[54] APPLE TREE NAMED 'AMBROSIA'

[75] Inventors: Wilfrid John Mennell; Sally Beth Mennell, both of Cawston, Canada

[73] Assignee: okanagan Plant Improvement Co. Ltd.

[21] Appl. No.: 879,121

[22] Filed: Jun. 19, 1997

[51] Int. Cl.[6] ..... A01H 5/00

[52] U.S. Cl. ..... Plt./34.1

[58] Field of Search ..... Plt./34.1

*Primary Examiner*—Howard J. Locker
*Assistant Examiner*—Melissa L. Kimball

[57] ABSTRACT

The present invention relates to an apple tree and more particularly to a new and distinct variety named 'Ambrosia', broadly characterized by its aroma, taste, color, shape, precocity and productivity. The variety has a distinct fruity aroma. The taste is very sweet and subacid. The flesh is firm and crisp in texture. The skin color has a high gloss, 70% to 90% bright red blush with broad faint stripes on a cream to yellow background. The fruit is conical and angular in shape with slight calyx lobing and a wide eye basin.

'Ambrosia' is a mid to late season apple maturing about the 16th to 21st of September at Cawston, British Columbia, Canada. 'Ambrosia' was discovered as a naturally occurring chance seedling in the cultivated orchard of Wilfrid and Sally Mennell at Cawston, British Columbia Canada.

2 Drawing Sheets

BACKGROUND OF THE INVENTION

This invention relates to apple trees and particularly to a chance seedling of unknown parentage discovered and evaluated by Wilfrid Mennell in the cultivated commercial orchard of Sally Mennell at Cawston, British Columbia, Canada.

We the inventors have been commercial producers, packers and shippers of various tree fruit varieties for many years and are constantly on the lookout for new varieties which may have commercial potential.

The variety presently to be described is such an apple and is of red blush with red stripes over cream to yellow background and sweet subacid taste differing from all known varieties.

This variety of unknown parentage, which may be the result of the parents, 'Starking Delicious'(unpatented) and 'Golden Delicious' (unpatented), closest resembles the commercial variety 'Jonagold'(unpatented).

Distinguishing Characteristics

'Ambrosia' differs from other dessert quality apple cultivars in the following distinctive combination of traits.

Under growing conditions at Cawston, British Columbia, Canada 'Ambrosia' has a distinct fruity aroma. The taste is sweet and subacid. The skin has a high gloss and 70% to 90% bright red blush with broad faint stripes on a cream to yellow background. The fruit shape is conical and angular, with slight calyx lobing and a wide eye basin. 'Ambrosia' is a mid to late season apple maturing approximately the 16th to 21 st of September at Cawston, B. C.

The tree is very precocious and bears moderate to heavy crop loads annually. Cropping begins in the 2nd or 3rd year. The tree shows more resistance to mildew than the reference varieties (commercial varieties).

Possible Parent Plants

'Starking Delicious' and 'Golden Delicious'.

The seedling tree was found in a cultivated plum orchard previously planted to 'Golden Delicious' and 'Starking Delicious'.

'Golden Delicious' was developed from a chance seedling discovered in Clay Creek, W. Va. by Andrew H. Mullins in 1914.

'Starking Delicious' was developed from a bud sport of a 'Delicious' tree discovered in Monroeville, New Jersey by Lewis Mood in 1921.

BRIEF DESCRIPTION OF THE DRAWINGS

The accompanying photographs show the mature fruit of 'Ambrosia'. The photographs show a typical limb, leaves and fruit.

The photograph on sheet 1 shows the typical mature fruit positioned to display stem end, calyx end and side view. The photograph also displays a cross sectional view to reveal the internal arrangement of the core, seeds and locules, and a longitudinal section to show the eye basin, stem bowl, core, and the color of the flesh and seeds.

The photographs on sheet 2 each illustrate the mature fruit prior to harvest; the lower photograph also illustrates the tree habit.

SUMMARY OF THE NEW VARIETY

'Ambrosia' was discovered and evaluated by Wilfrid Mennell as a naturally occurring chance seedling on the property of Sally Mennell at Cawston, British Columbia, Canada. 'Ambrosia' was asexually reproduced by budding in 1990 by Wilfrid Mennell. Evaluation upon fruiting showed the variety to be stable and no variations occurred. The resulting trees exhibited the same unique qualities as the original tree.

'Ambrosia' has medium to large fruit with skin color of red blush with faint, broad red stripes over a cream to yellow background. Fruit of 'Ambrosia' matures about the third week in September at Cawston, British Columbia, Canada.

'Golden Delicious' is a medium to large, yellow/green skinned variety maturing before 'Starking Delicious' and 'Ambrosia'.

'Starking Delicious' is a large to very large variety with skin of red striped overcolor on a green/yellow background. 'Starking Delicious' matures slightly before 'Ambrosia'.

Trials and Evaluations

The variety 'Ambrosia' was established from the novel seedling by asexual propagation (budding) in 1990 at the Mennell Orchards in Cawston British Columbia Canada by Wilfrid Mennell. The trees were planted in close proximity to the most similar variety, 'Jonagold', an established commercial variety. Evaluation began upon fruiting. Further family trials of the variety were planted in 1994, and controlled grower test sites were established in British Columbia and at the okanagan Plant Improvement Co. Ltd. test orchard at Oliver, British Columbia. It was found, through test plots, field evaluation, and sensory evaluation panels that the new variety exhibited the following unique combination of qualities:

Under growing conditions in Cawston B.C. 'Ambrosia' is a mid to late season apple maturing at approximately the same time as 'Jonagold' about the 16th to 21st of September, at Cawston, British Columbia, Canada. The fruit is sweet, subacid, crisp, very juicy and aromatic. The skin has a 70% to 90% red blush with broad, faint red striped overcolor on a cream to yellow background, whereas 'Jonagold' has a green to yellow background color with a 30% to 50% red blush and stripe overcolor at Cawston, B.C. The fruit of 'Ambrosia' is medium to large averaging 7.4 cm in diameter and averaging 210 to 220 grams in weight. The fruit of 'Jonagol' is large averaging 8.8 cm. in diameter and 245 to 255 grams in weight. The fruit of 'Ambrosia' is conical and angular in shape with medium calyx lobing whereas 'Jonagold' is of a more globose shape and has very slight calyx lobing. The eye a basin is deeper and wider in 'Ambrosia' than 'Jonagold'. The tree of 'Ambrosia' is vigorous with an upright spreading growth habit and is not a tip bearer. The tree is productive and precocious with spur type branches, producing good crops in the third year after planting. The tree produces good crops annually. 'Jonagold' trees are more spreading than 'Ambrosia' and more susceptible to mildew than is 'Ambrosia'. 'Ambrosia' does not show any unusual susceptibility to any diseases including fireblight and apple scab and observations to date indicate there may be some resistance to apple scab. The leaves of 'Ambrosia' have shallow crenate margins whereas 'Jonagold' has deeply serrated leaf margins. The skin of the fruit is smooth and very glossy. 'Ambrosia' flowers mid-season and produces medium pink and white flowers with broad elliptic petals. The petals of the flowers are touching.

Botanical description of the plant:

*'Ambrosia'*.—Genus: Malus. Species: ×*domestica*. Market class: Dessert. Parentage: Unknown. A naturally occurring chance seedling that was found in a cultivated orchard of Sally and Wilfrid Mennell possibly arising from a cross of 'Starking Delicious' and 'Golden Delicious'.

*'Starking Delicious'*.—Genus: Malus. Species: ×*domestica*. Market class: Dessert. Parentage: 'Starking Delicious' was developed from a bud sport of a 'Delicious' tree discovered in Monroeville, N.J. by Lewis Mood in 1921.

*'Golden Delicious'*.—Genus: Malus. Species: ×*domestica*. Market class: Dessert. Parentage: 'Golden Delicious' was developed from a chance seedling discovered in Clay Creek, W. Va. by Andrew H. Mullins in 1914.

The following is a detailed description of the new variety, with color terminology in accordance with The Royal Horticultural Society (R.H.S.) Colour Chart, except where general color terms of ordinary dictionary significance are suitable.

Pomological characteristics: 'Ambrosia'.

Fruit end use: Dessert.

Growth characteristics:

*Tree* (*Trees observed were of the same age on M*9 *rootstock*).—Vigor: Intermediate. Habit: Upright. Branch frequency: Medium. Branch strength: Intermediate. Angle of bearing branches: <90 Degrees. Predominance of bearing: Spurs.

*Shoot Characteristics* (*Observations done on one-year old dormant shoots in* 1996).—Pubescence (on upper half): Weak. Shine of bark: Medium. Mean diameter (center of middle internode): 5.5 mm. Mean internode length: 24.0mm. Flexibility: Medium flexibility. Number of lenticels (middle third of shoot): Medium to many. Size of lenticels: Large. Predominant color(on sunny side): Reddish-brown. Position of bud on shoot: Appressed. Shape of bud: Pointed.

*Flower characteristics* (*Measurements are means of* 10 *flowers*).—Type: Single. Size (pressed flat): 5.7cm. Color of bud (balloon stage): 60C/155D (R.H.S.). Bud burst: Early, with 'Mcintosh'. Petal shape: Broad elliptic. Petal margins: Touching.

*Leaf characteristics* (*Measurements are means of* 10 *fully expanded leaves* 4*th to* 6*th from the top of the shoot*).—Shape at cross section: Concave. Pubescence of upper side: Weak. Color upper side: 137A (R.H.S.). Veins: Some anthocyanin evident. Orientation: Up and out. Leaf length—Mean: 86 mm. —Range: 78–95 mm. Leaf width—Mean: 54 mm. —Range: 44–60 mm . Blade ratio (length/width): 1.62. Petiole length—Mean: 29 mm. — Range: 26–32 mm. Leaf length/petiole (ratio): 2.9. Glossiness of upper side: Medium. Pubescence on lower side: Pubescent. Stipule size—Mean: 10 mm. —Range: 12–20 mm.

*Fruit Characteristics* (*measurements are the means of* 10 *mature fruits*).—Size (diameter): 7.5 cm. Average fruit weight: 210–220 g. Shape: Globose conical . Symmetry (side view): Symmetrical . Ribbing: Present. Prominence of ribbing: Weak to medium. Distal end crowning: Present. Prominence of crowning: Medium. Aperture of eye: Open. Depth of eye basin: 11 mm. Width of eye basin: 31 mm. Sepal spacing: Free. Thickness of stalk: 2.3 mm. Stalk cavity width: 30 mm. Stalk length: 21 mm. Surface: Smooth. Bloom of skin: Absent. Waxiness of skin: Slight . Translucency of skin: Absent. Groundcolour: Cream to soft yellow. Amount of overcolor of skin: 70–90 %. Over color of skin (R.H.S.): Red (46A). Type of over color: Streaked and solid. Amount of russet: None. Position of russet: None. Size of lenticels on fruit: Small. Prominence of lenticels: Very slight. Color of flesh: Cream. Distinctness of core line (cross section): Weak. Aperture of locules: ½ open. Setting (yield efficiency): High. Maturity date: 3rd week of September at Cawston, B.C. Seed color at maturity: Brown. Juiciness: Medium to juicy. Flesh firmness without skin(Penetrometer): 15 lbs. Browning of flesh(1 hr. after cutting): Weak.

*Storage of fruit* (*Storage trials done by Okanacan Federated Shippers*).—Air: 4 months. Controlled Atmosphere: 6 months.

We claim:

1. A new and distinct variety of apple tree, originating as a chance seedling, substantially illustrated and described, which is most similar to 'Jonagold' and characterized as to novelty by the bright red blush with faint red striped overcolor on a cream to yellow background, the conical and angular shape, wide eye basin, and the unique combination of taste, texture and juiciness which are different from other dessert quality apples.

* * * * *

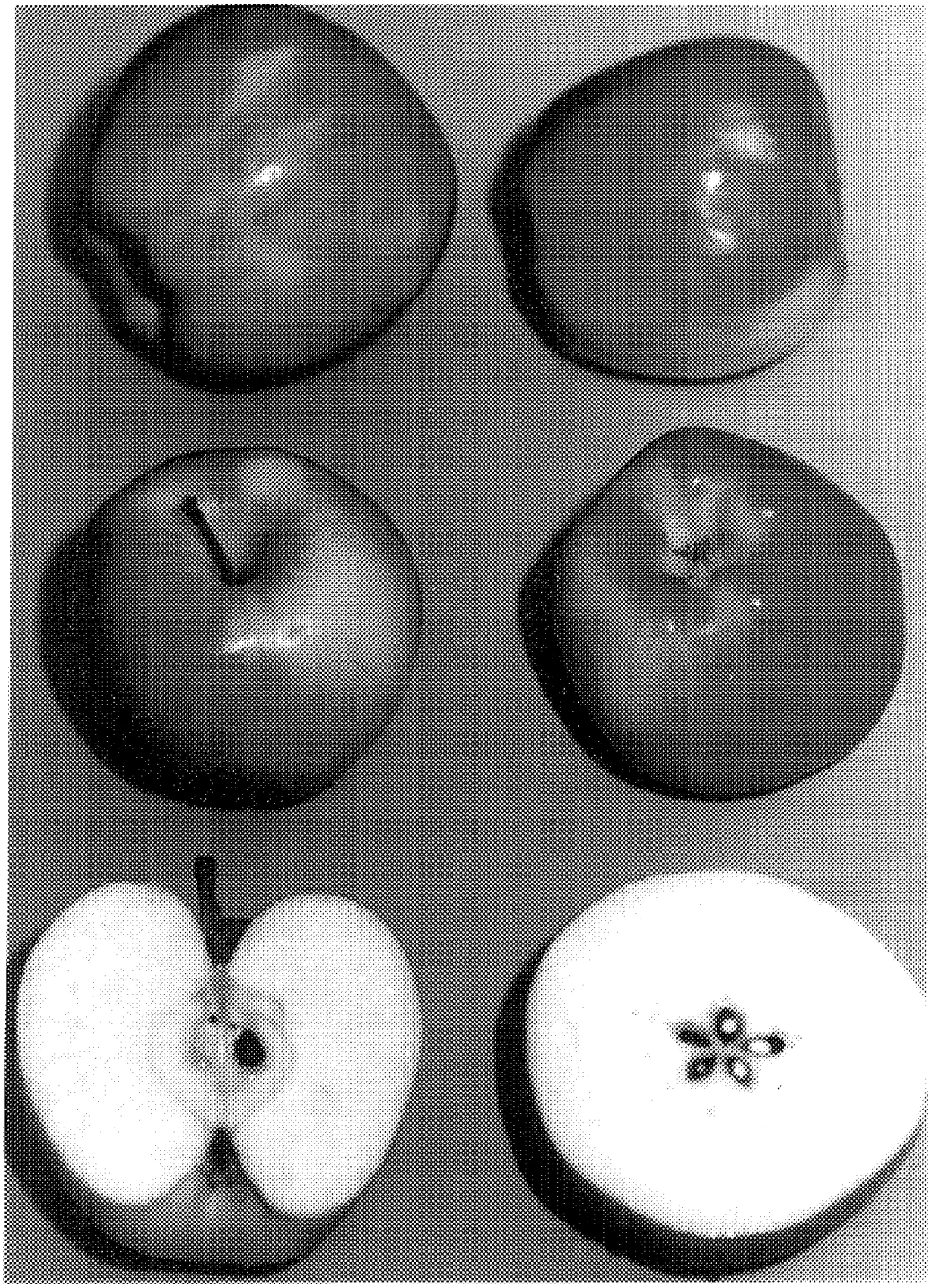

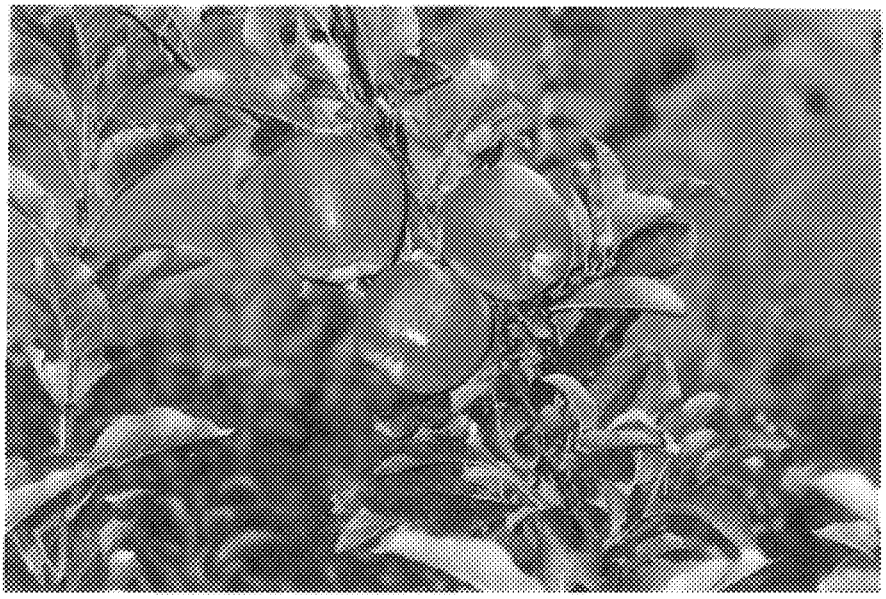
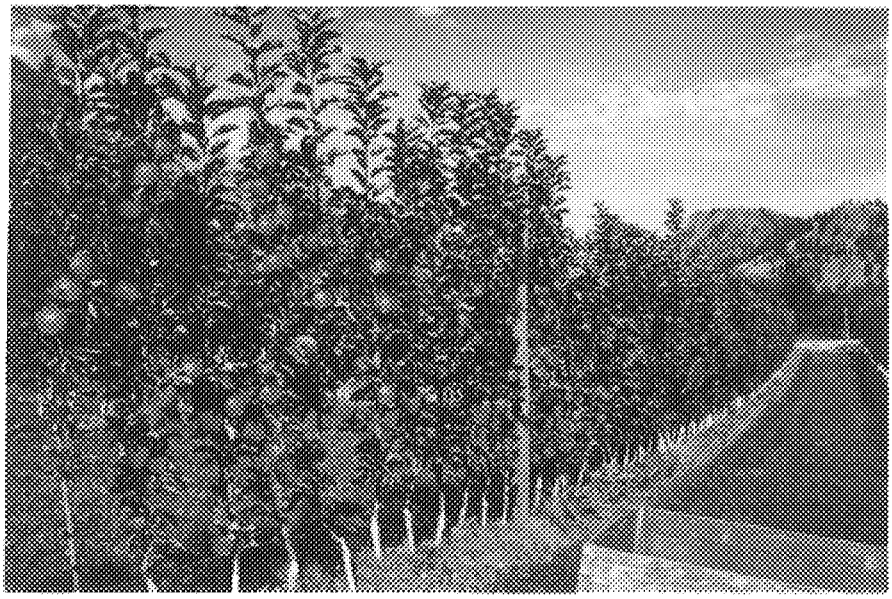

UNITED STATES PATENT AND TRADEMARK OFFICE

CERTIFICATE OF CORRECTION

PATENT NO. : PP 10,789 
DATED : February 16, 1999
INVENTOR(S) : Mennell, Wilfrid, John Mennell and Sally, Beth It is certified that error appears in the above-identified patent and that said Letters Patent is hereby corrected as shown below:

Title page,
Item [73], Assignee, delete "Okanagan Plant Improvement Co. Ltd"

Signed and Sealed this

Seventh Day of September, 2004

JON W. DUDAS
*Director of the United States Patent and Trademark Office*